(12) United States Patent
Liu et al.

(10) Patent No.: US 9,725,375 B2
(45) Date of Patent: *Aug. 8, 2017

(54) METHOD FOR PREPARING A LIGHT OLEFIN WITH AN OXYGEN-CONTAINING COMPOUND

(71) Applicant: DALIAN INSTITUTE OF CHEMICAL PHYSICS, CHINESE ACADEMY OF SCIENCES, Dalian (CN)

(72) Inventors: Zhongmin Liu, Dalian (CN); Mao Ye, Dalian (CN); Tao Zhang, Dalian (CN); Changqing He, Dalian (CN); Xiangao Wang, Dalian (CN); Yinfeng Zhao, Dalian (CN)

(73) Assignee: DALIAN INSTITUTE OF CHEMICAL PHYSICS, CHINESE ACADEMY OF SCIENCES, Dalian (CN)

(*) Notice: Subject to any disclaimer, the term of this patent is extended or adjusted under 35 U.S.C. 154(b) by 0 days.

This patent is subject to a terminal disclaimer.

(21) Appl. No.: 15/101,297

(22) PCT Filed: Dec. 3, 2013

(86) PCT No.: PCT/CN2013/088398
§ 371 (c)(1),
(2) Date: Jun. 2, 2016

(87) PCT Pub. No.: WO2015/081489
PCT Pub. Date: Jun. 11, 2015

(65) Prior Publication Data
US 2016/0304413 A1 Oct. 20, 2016

(51) Int. Cl.
*C07C 1/20* (2006.01)
*C07C 1/207* (2006.01)
(Continued)

(52) U.S. Cl.
CPC .............. *C07C 1/20* (2013.01); *B01J 29/90* (2013.01); *B01J 38/06* (2013.01); *B01J 38/12* (2013.01);
(Continued)

(58) Field of Classification Search
CPC C07C 1/20; C07C 1/207; C07C 1/213; C07C 1/24; C07C 1/247; B01J 38/30; B01J 38/34
(Continued)

(56) References Cited

U.S. PATENT DOCUMENTS

| 6,166,282 A | 12/2000 | Miller |
| 2005/0101816 A1 | 5/2005 | Xu et al. |

(Continued)

FOREIGN PATENT DOCUMENTS

| CN | 102276406 A | 12/2011 |
| CN | 102463138 A | 5/2012 |

(Continued)

OTHER PUBLICATIONS

Search Report for related Singapore Application No. 11201604429V issued by Intellectual Property Office of Singapore dated Sep. 1, 2016.
(Continued)

*Primary Examiner* — Thuan D Dang
(74) *Attorney, Agent, or Firm* — Enshan Hong; VLP Law Group LLP

(57) ABSTRACT

A method for improving the light olefin yield in the process of preparation of a light olefin using an oxygen-containing compound, more specifically, in which, a multi-stage dense phase fluidized bed comprising k secondary pre-carbon deposition zones (k≥1) and n secondary reaction zones (n≥1) is used as a reactor, and a multi-stage dense phase fluidized bed regenerator comprising m secondary regeneration zones
(Continued)

(m≥2) is used as a main equipment, and by re-refining hydrocarbons with four or more carbons obtained in the separation section, or adding naphtha, gasoline, condensate oil, light diesel oil, hydrogenation tail oil or kerosene in the reaction zone, the method primarily solves the problems in the prior art of the uniformity of carbon deposition amount and the carbon content of the catalyst being difficult to control, and the light olefin yield being low.

14 Claims, 5 Drawing Sheets

(51) Int. Cl.
  *C07C 1/213*  (2006.01)
  *C07C 1/24*  (2006.01)
  *C07C 1/247*  (2006.01)
  *B01J 38/30*  (2006.01)
  *B01J 38/34*  (2006.01)
  *B01J 29/90*  (2006.01)
  *B01J 38/06*  (2006.01)
  *B01J 38/12*  (2006.01)
  *C07C 5/333*  (2006.01)

(52) U.S. Cl.
  CPC ............... *C07C 5/333* (2013.01); *Y02P 20/52* (2015.11); *Y02P 20/584* (2015.11); *Y02P 30/42* (2015.11)

(58) Field of Classification Search
  USPC ............................... 585/639, 640; 502/41, 43
  See application file for complete search history.

(56) References Cited

U.S. PATENT DOCUMENTS

2006/0135834 A1* 6/2006 Xu ........................... C07C 1/20
                   585/639
2010/0331596 A1 12/2010 Xie et al.
2011/0152479 A1 6/2011 Nesterenko

FOREIGN PATENT DOCUMENTS

| CN | 102816591 A | 12/2012 |
| CN | 101402538 B | 1/2013 |
| CN | 102875289 A | 1/2013 |
| CN | 102875296 A | 1/2013 |
| EA | 200801961 A1 | 4/2009 |
| WO | 2012152258 A1 | 5/2012 |

OTHER PUBLICATIONS

Search Report for related Australian Application No. 2013407180 issued by Australian Intellectual Property Office dated Nov. 1, 2016.

Office Action for related Japan Application No. 2016-535-725 issued by Japan Patent Office dated Apr. 14, 2017.

Office Action for related Russian Application No. 2016126180 completed by Russian Intellectual Property Office dated Apr. 28, 2017.

* cited by examiner

C-C section

Front view          Left sectional view

METHOD FOR PREPARING A LIGHT OLEFIN WITH AN OXYGEN-CONTAINING COMPOUND

RELATED APPLICATIONS

This is a U.S. national stage of international application No. PCT/CN2013/088398 filed on Dec. 3, 2013.

TECHNICAL FIELD

The present disclosure relates to a method for preparing a light olefin with increased yield of light olefin.

BACKGROUND

Light olefins, i.e. ethylene and propylene, are two important kinds of basic chemical raw materials, and the demand thereof is increasing. Generally, ethylene and propylene are produced via a petroleum scheme. However, the costs for producing ethylene and propylene from petroleum resources are increasing due to limited supply and relatively high price of petroleum resources. In recent years, techniques for preparing ethylene and propylene by converting substituent raw materials have been greatly developed. More and more attentions have been paid to the process of methanol-to-olefins (MTO), and the production scale of megatonnage has been achieved. As the world economy develops, the demand for light olefins, particularly propylene, is increasing day by day. It is reported as the analysis of CMAI Corporation that the demand for ethylene will increase at an average rate of 4.3% per year and the demand for propylene will increase at an average rate of 4.4% per year until 2016. Due to high-speed increase of the economy in China, all of the annual increase rates of the demand for ethylene and propylene in China exceed the average level of the world.

In early 1980s, UCC Corporation successfully developed SAPO series molecular sieves. Among others, SAPO-34 molecular sieve catalyst exhibits excellent catalytic performance when it is used in MTO reaction, and has very high selectivity for light olefins and very high activity. However, after the catalyst has been used for a period of time, the activity is lost due to carbon deposition. A remarkable induction period is present in the use of the SAPO-34 molecular sieve catalyst. In the induction period, the selectivity for olefins is relatively low and the selectivity for alkanes is relatively high. As the reaction time increases, the selectivity for light olefins gradually increases. After the induction period, the catalyst maintains high selectivity and high activity in a certain period of time. With further prolong of the time, however, the activity of the catalyst rapidly decreases.

U.S. Pat. No. 6,166,282 discloses a technique and a reactor for converting methanol to light olefins, which use a fast fluidized bed reactor, wherein after the completion of a reaction in a dense phase reaction zone having a relatively low gas speed, the gas phase rises to a fast separation zone having an inner diameter which rapidly becomes smaller, and most of the entrained catalyst is preliminarily separated using a special gas-solid separation apparatus. Since the product gas and the catalyst are rapidly separated after reaction, a secondary reaction is effectively prevented. Upon analog computation, the inner diameter of the fast fluidized bed reactor and the catalyst inventory required are both greatly reduced, compared to the conventional bubbling fluidized bed reactors. However, the carbon based yields of light olefins in this method are all typically about 77%, and there are problems concerning relatively low yields of light olefins.

CN101402538B discloses a method for increasing the yield of light olefins. This method provides a second reaction zone on the upper part of a first reaction zone for converting methanol to light olefins, and the diameter of the second reaction zone is greater than that of the first reaction zone to increase the residence time of the product gas from the outlet of the first reaction zone in the second reaction zone, such that the unreacted methanol, the generated dimethyl ether, and hydrocarbons having 4 or more carbons continue to react so as to achieve the object of increasing the yield of light olefins. This method may increase the yield of light olefins to some extent. However, since the catalyst come out from the first reaction zone has already carried a relatively great amount of deposited carbon and relatively high catalyst activity is required to crack hydrocarbons having 4 or more carbons, the conversion efficiencies of hydrocarbons having 4 or more carbons in the second reaction zone in this method are still relatively low, leading to a lower yield of light olefins.

CN102276406A discloses a method for increasing the production of propylene. This technique provides three reaction zones, wherein a first fast bed reaction zone is used for converting methanol to olefins, and a lift pipe reaction zone and a second fast bed reaction zone are connected in series to convert ethylene, hydrocarbons having 4 or more carbons, and unreacted methanol or dimethyl ether. In this patent application, the residence times of substances, such as hydrocarbons having 4 or more carbons, etc., in the lift pipe reaction zone and in the second fast bed reaction zone are relatively short and the conversion efficiencies are relatively low, such that the yield of propylene is relatively low.

CN102875289A discloses a fluidized bed reaction device with a lift pipe reactor arranged therein, which is used for increasing the yield of light olefins. A first raw material is passed into a fluidized bed reaction zone and is brought into contact with a catalyst to generate a product comprising light olefins, and at the meanwhile a spent catalyst is formed; a part of the spent catalyst is passed into a regenerator for regeneration to form a regenerated catalyst, and the other part of the spent catalyst is passed into a lift pipe with an outlet end located inside the reaction zone and is brought into contact with a second raw material so as to lift the spent catalyst into the reaction zone; and the regenerated catalyst is returned to the reaction zone of the fluidized bed reactor. Since the reaction device disclosed in this patent application does not comprise a stripping portion, the spent catalyst will be passed into the regenerator with carrying a part of the product gas, which is combusted with oxygen to reduce the yield of light olefins.

The technique for preparing olefins from methanol disclosed in CN102875296A provides three reaction zones, which are a fast bed, a downer, and a lift pipe. Since the catalyst is circulated among the regenerator, the fast bed, the lift pipe, and the downer, the flow direction is extremely complicated, the distribution and the control of the flow rate are extremely difficult, and the activity of catalyst greatly varies.

As well known in the art, the selectivity for light olefins is closely associated with the amount of carbon deposition on the catalyst. A certain amount of carbon deposition on SAPO-34 catalyst is needed to ensure a high selectivity for light olefins. Main reactors used in current MTO process are fluidized beds. The fluidized bed is close to a perfect mixing flow reactor, which has a wide distribution of carbon deposition on catalyst and is not advantageous for increasing the selectivity for light olefins. Since the catalyst-to-alcohol ratio is very small and the coke yield is relatively low in the MTO process, in order to achieve a lager and controllable catalyst circulation volume, it is required to control the amount of carbon deposition and the uniformity of carbon content on the catalyst to a certain level in the regeneration zone, thereby achieving the object of controlling the amount of carbon deposition and the uniformity of carbon content on the catalyst in the reaction zone. Therefore, it is a key technique in the MTO process to control the amount of carbon deposition and the uniformity of carbon content of the catalyst in the reaction zone to a certain level.

Furthermore, in the process of preparation of a light olefin using methanol, byproduct such as a hydrocarbon with four or more carbons etc. will be produced inevitably, and the carbon-based selectivity for the hydrocarbon with four or more carbons is generally around 10 wt %. If these byproducts can be further converted into target product, the yield of light olefin and the economical efficiency of the process will be improved. Our research has demonstrated that carbon-free SAPO-34 molecular sieve catalyst has excellent effect when using in the preparation of a light olefin by conversion of a hydrocarbon with four or more carbons, and may achieve the pre-carbon deposition on the SAPO-34 molecular sieve catalyst, thereby improving its selectivity for light olefin. A light olefin is very sensitive to the process parameters such as reaction temperature etc. For example, the temperature for regenerating the catalyst is generally higher than 550° C., which is much higher than the temperature of reaction zone, and the local over-temperature at the inlet for regenerated catalyst would decrease the selectivity for light olefin.

The factors such as distribution non-uniformity of carbon deposition on catalyst, carbon content being difficult to control and large fluctuation of reaction temperature are all disadvantageous for the improvement of the light olefin yield. In order to solve the problems described above, some researchers propose the techniques, such as providing an upper and a lower reaction zones in a fluidized bed, two fluidized beds connected in series, and a fluidized bed, a lift pipe, and a downer connected in series, and certain advantageous effects have been obtained. However, the complexity and the difficulty for controlling the MTO process are increased at the meanwhile. The present disclosure provides a solution in which multiple secondary reaction zones (re-generation zones) are formed by providing inner members in the dense phase fluidized bed for improving the yield of light olefin.

SUMMARY OF THE DISCLOSURE

The technical problem to be solved by the present disclosure is the problem of low yield for light olefin existed in prior art, and the object is to provide a new method for improving the yield for light olefin. This method is used in the production of light olefins, and has the advantages of good uniformity of carbon deposition on catalyst, relatively high yield for light olefin, and good economical efficiency of the production process of light olefin.

In order to achieve the above object, the present disclosure provides a method for preparing a light olefin using an oxygen-containing compound, comprising the following steps:

step a) in which a hydrocarbon with four or more carbons is introduced from k feeding branch lines of pre-carbon deposition zone in parallel into k secondary pre-carbon deposition zones in a dense phase fluidized bed reactor, and is brought into contact with a completely regenerated and/or fresh catalyst, so as to be converted into a light olefin product-containing stream, while forming a pre-carbon deposited catalyst; wherein the catalyst is passed sequentially through $1^{st}$ to $k^{th}$ secondary pre-carbon deposition zones, with carbon content thereof increasing gradually; wherein the dense phase fluidized bed reactor is divided by a material flow controller into a pre-carbon deposition zone and a reaction zone; and wherein the pre-carbon deposition zone of the dense phase fluidized bed reactor is divided by a material flow controller into k secondary pre-carbon deposition zones, with $1^{st}$ to $k^{th}$ secondary pre-carbon deposition zones being connected in sequence;

step b) in which a raw material comprising the oxygen-containing compound is introduced from n feeding branch lines of reaction zone in parallel into n secondary reaction zones of the dense phase fluidized bed reactor, and is brought into contact with the pre-carbon deposited catalyst, to generate a light olefin product-containing stream and a spent catalyst; wherein the pre-carbon deposited catalyst flowed out from the $k^{th}$ secondary pre-carbon deposition zone is passed sequentially through $1^{st}$ to $n^{th}$ secondary reaction zones, with carbon content thereof increasing gradually; wherein the reaction zone of the dense phase fluidized bed reactor is divided by a material flow controller into n secondary reaction zones, with $1^{st}$ to $n^{th}$ secondary reaction zones being connected in sequence, and the $1^{st}$ secondary reaction zone being connected to the downstream of the $k^{th}$ secondary pre-carbon deposition zone;

step c) in which the light olefin product-containing stream flowed out from the pre-carbon deposition zone and reaction zone is separated from the entrained spent catalyst; the isolated spent catalyst is passed into the $n^{th}$ secondary reaction zone; and the light olefin product-containing stream is passed into a product separation section, in which the light olefin product is obtained by isolation and purification, and the hydrocarbon byproduct with four or more carbons obtained from the separation section is returned back to the pre-carbon deposition zone in the dense phase fluidized bed reactor;

step d) in which the spent catalyst flowed out from the $n^{th}$ secondary reaction zone, after being stripped and lifted, is passed into a dense phase fluidized bed regenerator for regeneration; said spent catalyst is passed sequentially through $1^{st}$ to $m^{th}$ secondary regeneration zones; a regeneration medium is introduced in parallel from m feeding branch lines of regeneration zone into the $1^{st}$ to $m^{th}$ secondary regeneration zones, and the spent catalyst is brought into contact with the regeneration medium, with the carbon content thereof decreasing gradually; the catalyst after the completion of regeneration is returned back to the $1^{st}$ secondary pre-carbon deposition zone via stripping and lifting; wherein the dense phase fluidized bed regenerator is divided by a material flow controller into m secondary regeneration zones, and $1^{st}$ to $m^{th}$ secondary regeneration zones are connected in sequence;

wherein k≥1, n≥1, and m≥2. More preferably, 4≥k≥2, 8≥n≥3, 8≥m≥3.

In a preferred embodiment, in the dense phase fluidized bed reactor, the apparent linear velocity of gas in the material flow controller is less than or equals to the minimum fluidizing velocity of the catalyst.

In a preferred embodiment, in the dense phase fluidized bed regenerator, the apparent linear velocity of gas in the material flow controller is less than or equals to the minimum fluidizing velocity of the catalyst.

In a preferred embodiment, the catalyst comprise SAPO-34 molecular sieve.

In a preferred embodiment, the reaction conditions in the dense phase fluidized bed reactor are as follows: the apparent linear velocity of gas in the pre-carbon deposition zone and reaction zone is 0.1-1.5 m/s, the reaction temperature of the pre-carbon deposition zone is 500-650° C., the reaction temperature in the reaction zone is 400-550° C., and the bed density of the dense phase fluidized bed reactor is 200-1200 kg/m$^3$.

In a preferred embodiment, the average amount of carbon deposition on catalyst is increased in sequence from the $1^{st}$ secondary pre-carbon deposition zone to $n^{th}$ secondary reaction zone in the dense phase fluidized bed reactor, wherein the average amount of carbon deposition on catalyst in the $k^{th}$ secondary pre-carbon deposition zone is 0.5-3 wt %, and the average amount of carbon deposition on catalyst in the $n^{th}$ secondary reaction zone is 7-10 wt %.

In a preferred embodiment, the reaction conditions in the regeneration zone of the dense phase fluidized bed are as follows: the apparent linear velocity of gas is 0.1-1.5 m/s, the reaction temperature is 500-700° C., and the bed density is 200-1200 kg/m$^3$.

In a preferred embodiment, the average amount of carbon deposition on catalyst is decreased in sequence from the $1^{st}$ to $m^{th}$ secondary regeneration zones of the dense phase fluidized bed regeneration zone, wherein the average amount of carbon deposition on catalyst in the $1^{st}$ secondary regeneration zone is 2-10 wt %, and the average amount of carbon deposition on catalyst in the $m^{th}$ secondary regeneration zone is 0-0.1 wt %.

In a preferred embodiment, the oxygen-containing compound is methanol and/or dimethyl ether; the light olefin is any one of ethylene, propylene or butylene, or a mixture thereof; the hydrocarbon with four or more carbons is any one of naphtha, gasoline, condensate oil, light diesel oil, hydrogenation tail oil or kerosene, or a mixture thereof; and the regeneration medium is any one of air, oxygen-deficient air or water vapor, or a mixture thereof.

In a preferred embodiment, the catalyst after the completion of regeneration in step d) is subsequently returned back to the $1^{st}$ secondary pre-carbon deposition zone of the dense phase fluidized bed via stripping and lifting, wherein the lifting gas in the lifting process is any one of water vapor, a hydrocarbon with four or more carbons, naphtha, gasoline, condensate oil, light diesel oil, hydrogenation tail oil or kerosene, or a mixture thereof.

The method of the present disclosure not only effectively improves the yield of the target product of light olefin, but also optimizes the distribution and utilization of energy.

Figure 1:
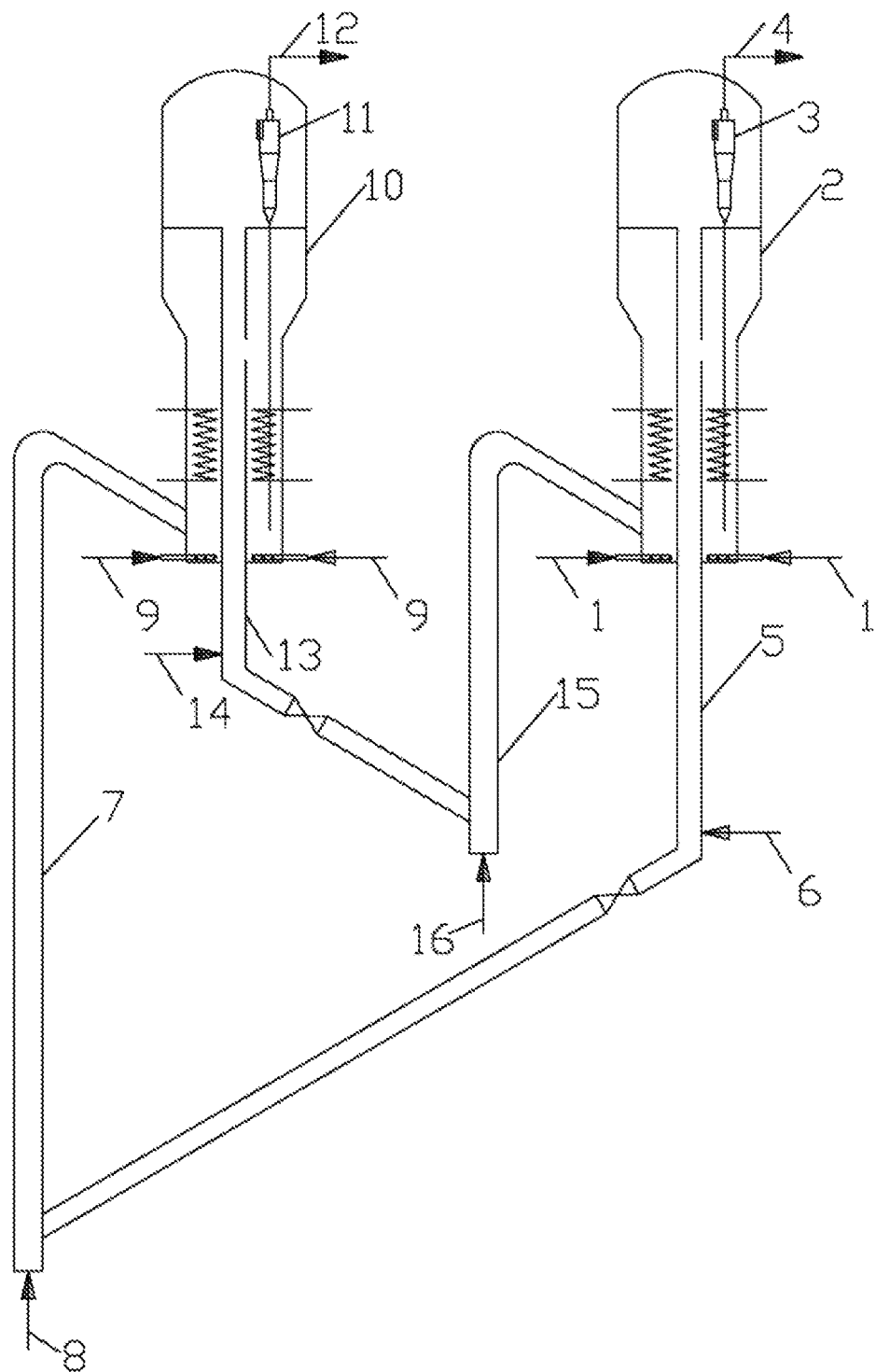
FIG. 1 is a schematic flow chart of the method in the present disclosure.

1: reactor feed line; 1-1: feeding branch line of $1^{st}$ secondary pre-carbon deposition zone; 1-2: feeding branch line of $2^{nd}$ secondary pre-carbon deposition zone; 1-3: feeding branch line of $1^{st}$ secondary reaction zone; 1-4: feeding branch line of $2^{nd}$ secondary reaction zone; 2: dense phase fluidized bed reactor; 2-1: $1^{st}$ secondary pre-carbon deposition zone; 2-2: $2^{nd}$ secondary pre-carbon deposition zone; 2-3: $1^{st}$ secondary reaction zone; 2-4: $2^{nd}$ secondary reaction zone; 3-cyclone separator; 4: product material line; 5: stripper; 6; water vapor line; 7: lift pipe; 8: lifting gas line; 9: regenerator feed line; 9-1: feeding branch line of $1^{st}$ secondary regeneration zone; 9-2: feeding branch line of $2^{nd}$ secondary regeneration zone; 9-3: feeding branch line of $3^{rd}$ secondary regeneration zone; 9-4: feeding branch line of $4^{th}$ secondary regeneration zone; 10: dense phase fluidized bed regenerator; 10-1: $1^{st}$ secondary regeneration zone; 10-2: $2^{nd}$ secondary regeneration zone; 10-3: $3^{rd}$ secondary regeneration zone; 10-4: $4^{th}$ secondary regeneration zone; 11: cyclone separator; 12: exhaust gas line; 13: stripper; 14: water vapor line; 15: lift pipe; 16: lifting gas line; 17: material flow controller; 18: material overflow port; 19: partition plate; 20: orifice; 21: material downward flow pipe; 22: bottom baffle; 23: heat extraction member.

DESCRIPTION OF THE PREFERRED EMBODIMENTS

In order to improve the light olefin yield in the process for preparing a light olefin using an oxygen-containing compound, the method provided in the present disclosure mainly comprises the following steps:

a) a step in which a hydrocarbon with four or more carbons is introduced from k feeding branch lines of pre-carbon deposition zone in parallel into k secondary pre-carbon deposition zones in a dense phase fluidized bed reactor, and is brought into contact with a completely regenerated and/or fresh catalyst, so as to be converted into a light olefin product-containing stream, while forming a pre-carbon deposited catalyst; wherein the catalyst is passed sequentially through $1^{st}$ to $k^{th}$ secondary pre-carbon deposition zones, with carbon content thereof increasing gradually; wherein the dense phase fluidized bed reactor is divided by a material flow controller into a pre-carbon deposition zone and a reaction zone; and wherein the pre-carbon deposition zone of the dense phase fluidized bed reactor is divided by a material flow controller into k secondary pre-carbon deposition zones, with $1^{st}$ to $k^{th}$ secondary pre-carbon deposition zones being connected in sequence;

b) a step in which a raw material comprising the oxygen-containing compound is introduced from n feeding branch lines of reaction zone in parallel into n secondary reaction zones of the dense phase fluidized bed reactor, and is brought into contact with the pre-carbon deposited catalyst, to generate a light olefin product-containing stream and a spent catalyst; wherein the pre-carbon deposited catalyst flowed out from the $k^{th}$ secondary pre-carbon deposition zone is passed sequentially through $1^{st}$ to $n^{th}$ secondary reaction zones, with carbon content thereof increasing gradually;

wherein the reaction zone of the dense phase fluidized bed reactor is divided by a material flow controller into n secondary reaction zones, with $1^{st}$ to $n^{th}$ secondary reaction zones being connected in sequence, and the $1^{st}$ secondary reaction zone being connected to the downstream of the $k^{th}$ secondary pre-carbon deposition zone;

c) a step in which the light olefin product-containing stream flowed out from the pre-carbon deposition zone and reaction zone is separated from the entrained spent catalyst; the isolated spent catalyst is passed into the $n^{th}$ secondary reaction zone; and the light olefin product-containing stream is passed into a product separation section, in which the light olefin product is obtained by isolation and purification, and the hydrocarbon byproduct with four or more carbons obtained from the separation section is returned back to the pre-carbon deposition zone in the dense phase fluidized bed reactor;

d) a step in which the spent catalyst flowed out from the $n^{th}$ secondary reaction zone, after being stripped and lifted, is passed into a dense phase fluidized bed regenerator for regeneration; said spent catalyst is passed sequentially through $1^{st}$ to $m^{th}$ secondary regeneration zones; a regeneration medium is introduced in parallel from m feeding branch lines of regeneration zone into the $1^{st}$ to $m^{th}$ secondary regeneration zones, and the spent catalyst is brought into contact with the regeneration medium, with the carbon content thereof decreasing gradually; the catalyst after the completion of regeneration is returned back to the $1^{st}$ secondary pre-carbon deposition zone via stripping and lifting; wherein the dense phase fluidized bed regenerator is divided by a material flow controller into m secondary regeneration zones, and $1^{st}$ to $m^{th}$ secondary regeneration zones are connected in sequence.

Preferably, the catalyst after the completion of regeneration in step d) is subsequently returned back to the $1^{st}$ secondary pre-carbon deposition zone of the dense phase fluidized bed via stripping and lifting, wherein the lifting gas in the lifting process is any one of water vapor, a hydrocarbon with four or more carbons, naphtha, gasoline, condensate oil, light diesel oil, hydrogenation tail oil or kerosene, or a mixture thereof.

Preferably, $k \geq 1$, $n \geq 1$, $m \geq 2$. Preferably, $4 \geq k \geq 2$, $8 \geq n \geq 3$, $8 \geq m \geq 3$.

Preferably, in the dense phase fluidized bed reactor, the apparent linear velocity of gas in the material flow controller is less than or equals to the minimum fluidizing velocity of the catalyst.

Preferably, in the dense phase fluidized bed regenerator, the apparent linear velocity of gas in the material flow controller is less than or equals to the minimum fluidizing velocity of the catalyst.

Preferably, the catalyst comprises SAPO-34 molecular sieve.

Preferably, the reaction conditions of the dense phase fluidized bed reactor are as follows: the apparent linear velocity of gas in the pre-carbon deposition zone and the reaction zone is 0.1-1.5 m/s, the reaction temperature in the pre-carbon deposition zone is 500-650° C., the reaction temperature of the reaction zone is 400-550° C., and the bed density is 200-1200 kg/m$^3$. Preferably, the average amount of carbon deposition on catalyst is increased in sequence from the 1st secondary pre-carbon deposition zone to $n^{th}$ secondary reaction zone in the dense phase fluidized bed reactor, wherein the average amount of carbon deposition on catalyst in the $k^{th}$ secondary pre-carbon deposition zone is 0.5-3 wt %, and the average amount of carbon deposition on catalyst in the $n^{th}$ secondary reaction zone is 7-10 wt %.

Preferably, the reaction conditions in the regeneration zone of the dense phase fluidized bed are as follows: the apparent linear velocity of gas is 0.1-1.5 m/s, the reaction temperature is 500-700° C., and the bed density is 200-1200 kg/m$^3$.

Preferably, the average amount of carbon deposition on catalyst is decreased in sequence from the $1^{st}$ to $m^{th}$ secondary regeneration zones of the regeneration zone of the dense phase fluidized bed, wherein the average amount of carbon deposition on catalyst in the $1^{st}$ secondary regeneration zone is 2-10 wt %, and the average amount of carbon deposition on catalyst in the $m^{th}$ secondary regeneration zone is 0-0.1 wt %.

Preferably, the oxygen-containing compound is methanol and/or dimethyl ether; the light olefin is any one of ethylene, propylene or butylene, or a mixture thereof; and the hydrocarbon with four or more carbons is any one of naphtha, gasoline, condensate oil, light diesel oil, hydrogenation tail oil or kerosene, or a mixture thereof.

The technical solution provided in the present disclosure further comprises (1) providing a dense phase fluidized bed reactor, comprising a pre-carbon deposition zone, a reaction zone, a gas-solid separation zone, and a stripping zone. The pre-carbon deposition zone and the reaction zone are divided by a material flow controller, wherein the pre-carbon deposition zone is divided by a material flow controller into k secondary pre-carbon deposition zones, $k \geq 1$, and the reaction zone is divided by a material flow controller into n secondary reaction zones, $n \geq 1$, each of the secondary pre-carbon deposition zones and the secondary reaction zones can be fed independently;

(2) providing a dense phase fluidized bed regenerator, comprising a regeneration zone, a gas-solid separation zone, and a stripping zone, wherein the regeneration zone is divided by a material flow controller into m secondary regeneration zones, $m \geq 2$, and each of the secondary regeneration zones can be fed independently.

Preferably, the hydrocarbon with four or more carbons etc. are passed in parallel into k secondary pre-carbon deposition zones in the dense phase fluidized bed reactor, and are brought into contact with the completely regenerated catalyst, so as to be converted into a light olefin product-containing stream. Meanwhile, the catalyst is passed sequentially through $1^{st}$ to $k^{th}$ secondary pre-carbon deposition zone, and forms the pre-carbon deposited catalyst when the carbon deposition amount reaches to a certain level, and then pre-carbon deposited catalyst is passed into reaction zone.

Preferably, the raw material comprising an oxygen-containing compound is passed in parallel into $n^{th}$ secondary reaction zone in the dense phase fluidized bed reactor and is brought into contact with the pre-carbon deposited catalyst, to generate a light olefin product-containing stream and a spent catalyst, meanwhile, the pre-carbon deposited catalyst is passed sequentially through $1^{st}$ to $n^{th}$ secondary reaction zones, with carbon content thereof increasing gradually.

Preferably, via stripping and lifting, the spent catalyst flowing out from $n^{th}$ secondary reaction zone is passed into the dense phase fluidized bed regenerator for regeneration, the spent catalyst is passed sequentially through is $1^{st}$ to $m^{th}$ secondary regeneration zones, and is brought into contact with the regeneration medium, with the carbon content gradually decreasing to near zero, and then is returned back to $1^{st}$ secondary pre-carbon deposition zone via stripping and lifting.

Preferably, the light olefin product stream is passed into separation section after separation with the entrained spent catalyst, and the isolated spent catalyst is passed into $n^{th}$ secondary reaction zone;

Preferably, the byproduct of hydrocarbon with four or more carbons obtained in the separation section is returned back to the pre-carbon deposition zone of the dense phase fluidized bed reactor.

In a preferred embodiment, the schematic flow chart of the method for improving the light olefin yield in the preparation of the light olefin using an oxygen-containing compound in the present disclosure is as shown in FIG. 1. The hydrocarbon with four or more carbons is introduced from the feeding branch lines (1-1, 1-2) of the pre-carbon deposition zone in parallel into the secondary pre-carbon deposition zones (2-1, 2-2) in the dense phase fluidized bed reactor (2), and is brought into contact with a catalyst comprising SAPO-34 molecular sieve, to generate a gas phase product-containing stream and a pre-carbon deposited catalyst; a raw material comprising the oxygen-containing compound is introduced from the feeding branch lines (1-3, 1-4) of reaction zone in parallel into the secondary reaction zones (2-3, 2-4) in the dense phase fluidized bed reactor (2), and is brought into contact with the pre-carbon deposited catalyst, generating a gas phase product stream and a spent catalyst; the gas phase product stream from the pre-carbon deposition zone and the reaction zone and the entrained catalyst are passed into a cyclone separator (3), wherein the gas phase product material flows through the outlet of the cyclone separator and the product material line (4) and enters into the subsequent separation section, the entrained catalyst is passed into $2^{nd}$ secondary reaction zone (2-4) via the dipleg of the cyclone separator; the regenerated catalyst from the dense phase fluidized bed regenerator (10) is passed into a dense phase fluidized bed reactor (2) via a stripper (13) and a lift pipe (15), wherein the bottom of the stripper (13) is connected to a water vapor line (14), and the bottom of the lift pipe (15) is connected to a lifting gas line (16); in the dense phase fluidized bed reactor (2), the regenerated catalyst is passed sequentially through $1^{st}$ secondary pre-carbon deposition zone to $2^{nd}$ secondary reaction zone (2-1, . . . , 2-4), and forms the spent catalyst after carbon deposition; the regeneration medium is introduced in parallel from the regenerator feed line (9) and the branch lines (9-1, . . . , 9-4) thereof into the secondary regeneration zones (10-1, . . . , 10-4) in the dense phase fluidized bed regenerator (10), and is brought into contact with the spent catalyst, to generate exhaust gas and regenerated catalyst after charking, and then the exhaust gas and the entrained regenerated catalyst are passed into a cyclone separator (11), from which, the exhaust gas is passed into a tail gas processing section through the outlet of the cyclone separator and exhaust gas line (12), and is emitted after processing, and the entrained regenerated catalyst is passed into $4^{th}$ secondary regeneration zone (10-4) via the dipleg of the cyclone separator; the spent catalyst from the dense phase fluidized bed reactor (2) is passed into the dense phase fluidized bed regenerator (10) via a stripper (5) and a lift pipe (7), wherein the bottom of the stripper (5) is connected to a water vapor line (6), and the bottom of the lift pipe (7) is connected to a lifting gas line (8); in the dense phase fluidized bed regenerator (10), the spent catalyst is passed sequentially through $1^{st}$ to $4^{th}$ secondary regeneration zones (10-1, . . . , 10-4), and the regenerated catalyst is formed after charking. The lifting gas in the lift pipe (7) may be any one of water vapor, a hydrocarbon with four or more carbons, naphtha, gasoline, condensate oil, light diesel oil, hydrogenation tail oil or kerosene, or a mixture thereof.

Figure 2:
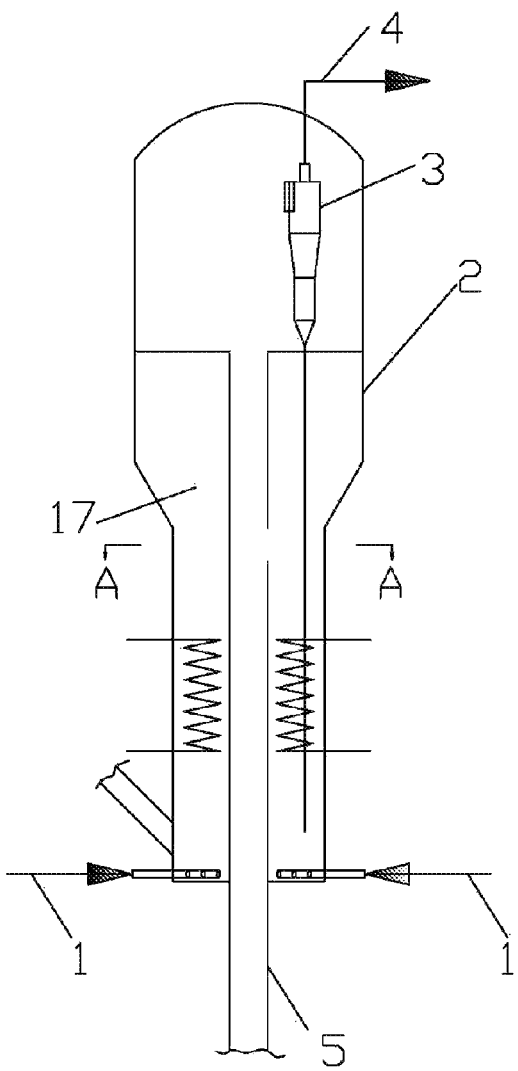
FIG. 2 is a structural schematic diagram of the dense phase fluidized bed comprising 2 secondary pre-carbon deposition zones and 2 secondary reaction zones in the present disclosure, wherein the arrows in the A-A sectional view show the flow direction of the catalyst between the secondary pre-carbon deposition zones and the secondary reaction zones.
Figure 2:
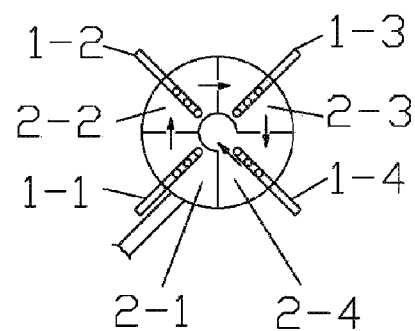

In a specific embodiment, the structural schematic diagram of the dense phase fluidized bed reactor comprising 2 secondary pre-carbon deposition zones and 2 secondary reaction zones in the present disclosure is shown in FIG. 2. Three material flow controllers (17) and one baffle are provided vertically to form 2 secondary pre-carbon deposition zones and 2 secondary reaction zones. The catalyst is passed sequentially through $1^{st}$ secondary pre-carbon deposition zone, $2^{nd}$ secondary pre-carbon deposition zone, $1^{st}$ secondary reaction zone, $2^{nd}$ secondary reaction zone, and is then passed into the stripper.

Figure 3:
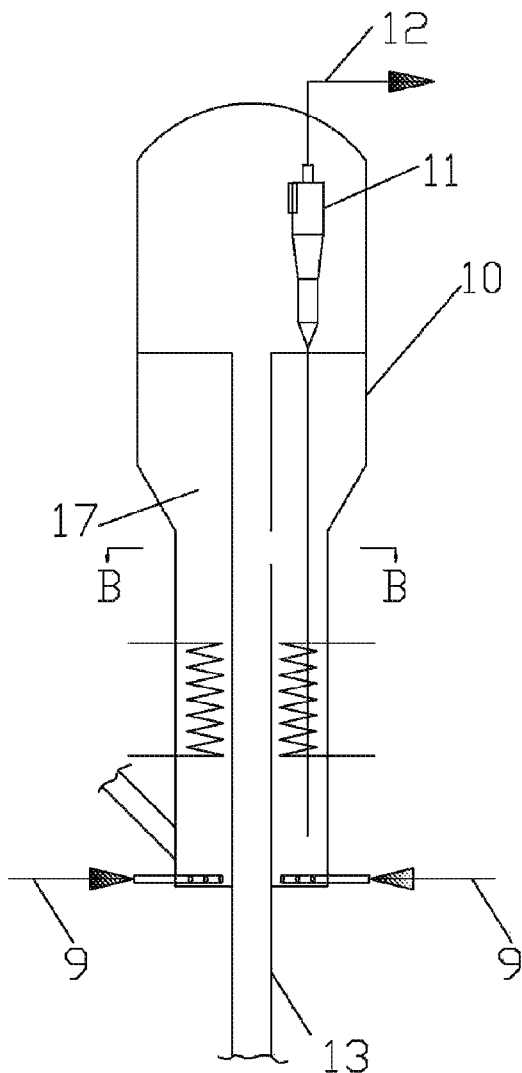
FIG. 3 is a structural schematic diagram of the dense phase fluidized bed comprising 4 secondary regeneration zones in the present disclosure, wherein the arrows in B-B sectional view show the flow direction of the catalyst between the secondary regeneration zones.
Figure 3:
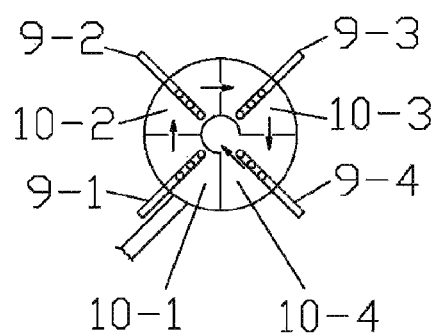

In a specific embodiment, the structural schematic diagram of the dense phase fluidized bed regenerator comprising 4 secondary regeneration zones in the present disclosure is as shown in FIG. 3. Three material flow controllers (17) and one baffle are vertically provided to separate the regeneration zone into 4 secondary regeneration zones. The catalyst is passed sequentially through the $1^{st}$ to the $4^{th}$ secondary regeneration zones and is then passed into the stripper.

Figure 4:
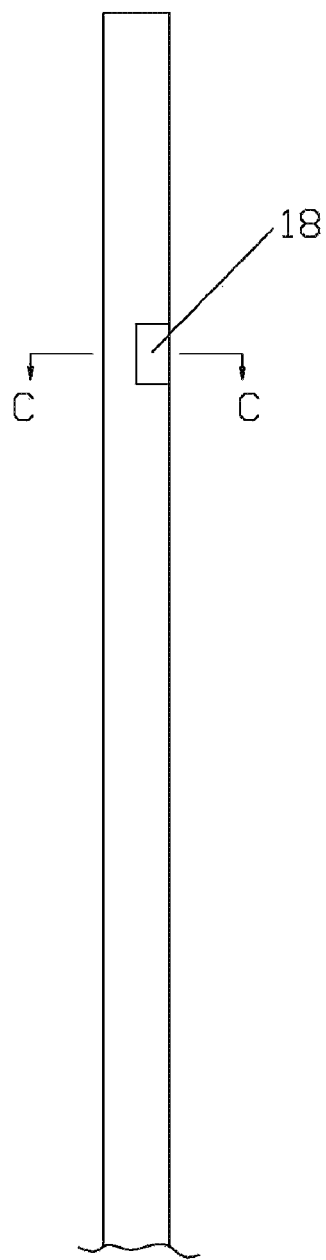
FIG. 4 is a structural schematic diagram of the stripper in the present disclosure.
Figure 4:

In a specific embodiment, the structural schematic diagram of the stripper in the present disclosure is as shown in FIG. 4. The opening on the tube wall on the upper part of the stripper is a material overflow port (18) between $n^{th}$ secondary reaction zone (or $m^{th}$ secondary regeneration zone) and the stripper.

Figure 5:
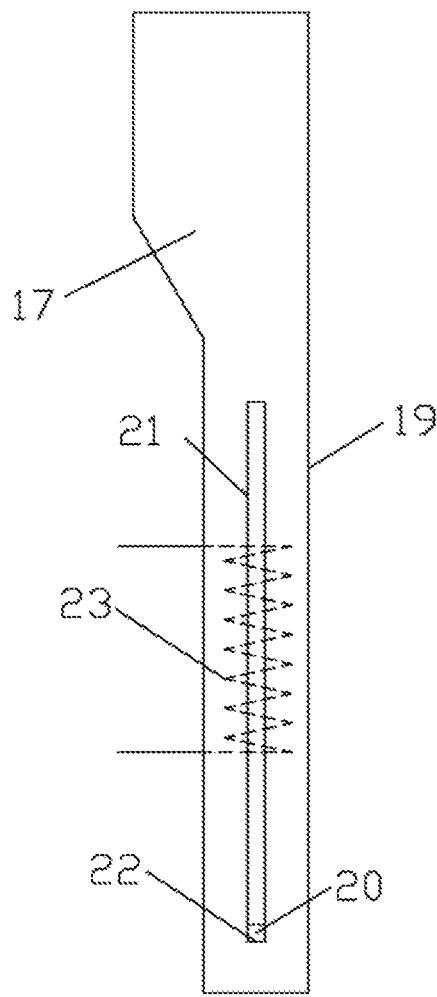
FIG. 5 is a structural schematic diagram of the material flow controller in the present disclosure.
Figure 5:
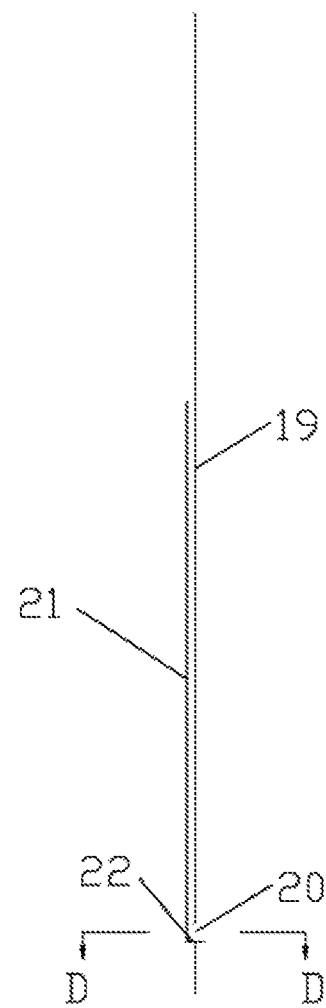
Figure 5:
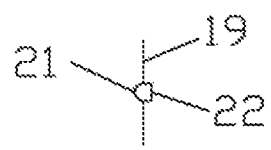

In a specific embodiment, the structural schematic diagram of the material flow controller in the present disclosure is as shown in FIG. 5. The material flow controller (17) is composed of a partition plate (19), an orifice (20), a material downward flow pipe (21), a bottom baffle (22) and a heat extraction member (23). The catalyst is passed into the material downward flow pipe from the top of the downward flow pipe, wherein the apparent linear velocity of gas is less than or equals to the minimal fluidizing velocity, the catalyst in the material downward flow pipe is in a dense phase packing state, and a material flow driving force is formed to drive the catalyst to flow into a next secondary pre-carbon deposition zone (or reaction zone, or regeneration zone) via the orifice. A coil structure may be used as the heat extraction member, which is fixed onto the partition plate.

Preferably, the apparent linear velocity of gas within the pre-carbon deposition zone and the reaction zone in the dense phase fluidized bed reactor is 0.1-1.5 m/s; the apparent linear velocity of gas within the regeneration zone is in the dense phase fluidized bed is 0.1-1.5 m/s; the apparent linear velocity of gas in the material flow controller is less than or equals to the minimum fluidizing velocity of the catalyst; the catalyst comprises SAPO-34 molecular sieve; k feed inlets are provided at the bottom of the pre-carbon deposition zone, in which the feed includes a hydrocarbon with four or more carbons, naphtha, gasoline etc.; n feed inlets are provided at the bottom of the reaction zone, in which the feed includes methanol, dimethyl ether etc.; the stripping medium in the stripping zone comprises water vapor; the inlet for the regeneration medium is provided at the bottom of the regeneration zone, the regeneration medium including air, oxygen-deficient air, water vapor etc.; the reaction temperature in the pre-carbon deposition zone is 500-650° C., the reaction temperature in the reaction zone is 400-550° C., the bed density of the pre-carbon deposition zone and the reaction zone is 200-1200 kg/m³, the average amounts of carbon deposition on catalyst in $1^{st}$ secondary pre-carbon deposition zone to $n^{th}$ secondary reaction zone increase in sequence, wherein the average amount of carbon deposition in k secondary pre-carbon deposition zones is 0.5-3 wt %, and the average amount of carbon deposition in $n^{th}$ secondary reaction zone is 7-10 wt %; the reaction temperature of the regeneration zone is 500-700° C., the bed density is 200-1200 kg/m³, the average amounts of carbon deposition on catalyst in $1^{st}$ to $m^{th}$ secondary regeneration zones decrease in sequence, wherein the average amount of carbon deposition in $1^{st}$ secondary regeneration zone is 2-10 wt %, and the average amount of carbon deposition in $m^{th}$ secondary regeneration zone is 0-0.1 wt %.

Preferably, instead of a hydrocarbon with four or more carbons, naphtha, gasoline, condensate oil, light diesel oil, hydrogenation tail oil or/and kerosene may also be used as raw materials in the pre-carbon deposition zone of the dense phase fluidized bed reactor of the present disclosure. These hydrocarbons also have the effect of lowering the temperature of regenerated catalyst and pre-carbon depositing on the regenerated catalyst.

Preferably, the lifting gas in the lift pipe (15) may be water vapor, a hydrocarbon with four or more carbons, naphtha, gasoline, condensate oil, light diesel oil, hydrogenation tail oil or/and kerosene. Using the method of the present disclosure, the objects of controlling the amount of carbon deposition on catalyst, improving the uniformity of carbon content and increasing the light olefin yield can be achieved. Therefore, it has significant technical advantages, and is useful in the industrial production of light olefins.

The advantageous effects that can be produced by the present disclosure include the following aspects: (1) the dense phase fluidized bed has a relatively high bed density, a relatively low catalyst velocity, and a low abrasion; (2) the gas velocity in the material downward flow pipe of the material flow controller is less than or equals to the minimal fluidization velocity of the catalyst, and the catalyst is in a dense phase packing state, such that a unidirectional dense phase conveying stream of the catalyst is formed, the backmixing of catalyst between adjacent secondary reaction zones (or adjacent secondary regeneration zones) is prevented, and the distribution of residence time is narrow; (3) the heat extraction member in the material flow controller has an effect of controlling the temperature of the reaction zone; (4) by means of material flow controller, the dense phase fluidized bed reactor is divided by into a pre-carbon deposition zone and a reaction zone, and the pre-carbon deposition zone is divided into k secondary pre-carbon deposition zones, the reaction zone is divided into n secondary reaction zones, wherein the catalyst is passed sequentially through $1^{st}$ secondary pre-carbon deposition zone to $n^{th}$ secondary reaction zone, such that the distribution of residence time is narrow and the uniformity of carbon content of the pre-carbon deposited catalyst and of spent catalyst is greatly increased; (5) the regenerated catalyst with high activity and high temperature is returned back to the $1^{st}$ secondary pre-carbon deposition zone, which facilitates the conversion of the hydrocarbon with four or more carbons to a light olefin, and after the reaction, the amount of the carbon deposition on the regenerated catalyst reaches to a certain level such that its selectivity for light olefin in the MTO reaction is also improved; (6) the conversion reaction of the hydrocarbon with four or more carbons into a light olefin occurred in the pre-carbon deposition zone is an endothermic reaction, which lowers the temperature of the regenerated catalyst, reliefs the heat extraction burden in the reaction zone, and effectively utilizes the heat, in the meantime, the contact between the high temperature catalyst and the oxygen-containing compound is avoid; (7) the regeneration zone is divided by a material flow controller into m secondary regeneration zones, and the spent catalyst is passed through $1^{st}$ to $m^{th}$ secondary regeneration zones in sequence, such that the distribution of residence time is narrow and the amount of the carbon deposition on the regenerated catalyst obtained after charking is close to zero; (8) all of the k secondary pre-carbon deposition zones, n secondary reaction zones and m secondary regeneration zones can be fed independently, with good flexibility of operation; (9) relatively precise control of carbon content of the regenerated catalyst and the spent catalyst is achieved, the distribution of carbon content is relatively uniform, the selectivity for light olefin is increased, and the carbon content may be regulated as needed to optimize the ratio of propylene/ethylene; (10) since the distribution of carbon content of the catalyst is relatively uniform, the catalyst inventory required in the reaction zone decreases; (11) the configuration of multiple secondary pre-carbon deposition zone, reaction zone, regeneration zone facilitates the achievement of large-scale reactors.

For better illustrating the present disclosure, and facilitating the understanding of the technical solution of the present disclosure, the exemplary and non-limiting examples in the present disclosure are provided as follows.

EXAMPLE 1

1 secondary pre-carbon deposition zone and 3 secondary reaction zones were provided in the dense phase fluidized bed reactor and 4 secondary regeneration zones were provided in the dense phase fluidized bed regenerator. Hydrocarbon with four or more carbons etc. was passed into $1^{st}$ secondary pre-carbon deposition zone of the dense phase fluidized bed reactor, and was brought into contact with the completely regenerated catalyst, converting into a product comprising a light olefin, in the meantime, allowing the amount of carbon deposition on the catalyst reach to a certain value, to form a pre-carbon deposited catalyst, which was then passed into the reaction zone; a raw material comprising an oxygen-containing compound was passed in parallel into $1^{st}$ to $3^{rd}$ secondary reaction zones in the dense phase fluidized bed reactor, while the pre-carbon deposited catalyst was passed sequentially through $1^{st}$ to $3^{rd}$ secondary reaction zones, wherein the raw material comprising an oxygen-containing compound was brought into contact with the pre-carbon deposited catalyst, to generate a product comprising a light olefin and inactivated spent catalyst; the stream of the gas phase product comprising a light olefin and the entrained spent catalyst were passed into a cyclone separator, from which, the gas phase product stream was passed into a subsequent separation section via the outlet of the cyclone separator, and the entrained spent catalyst was passed into $3^{rd}$ secondary reaction zone via the dipleg of the cyclone separator; via a stripper and a lift pipe, the spent catalyst from the $3^{rd}$ secondary reaction zone was passed into the dense phase fluidized bed regenerator, in which the spent catalyst was passed sequentially through $1^{st}$ to $4^{th}$ secondary regeneration zones, and was brought into contact with the regeneration medium, resulting in the regenerated catalyst after reaction; the regenerated catalyst was passed into the dense phase fluidized bed reactor again through a stripper and a lift pipe, and was passed sequentially through $1^{st}$ secondary pre-carbon deposition zone, $1^{st}$ secondary reaction zone to $4^{th}$ secondary reaction zone; the byproduct of hydrocarbon with four or more carbons obtained from the separation section was returned back to $1^{st}$ secondary pre-carbon deposition zone in the dense phase fluidized bed reactor; the lifting gas in the lift pipe 15 was a hydrocarbon with four or more carbons. The reaction conditions in the dense phase fluidized bed reactor were as follows: the temperature in $1^{st}$ secondary pre-carbon deposition zone was 500° C., the temperature in $1^{st}$ to $3^{rd}$ secondary reaction zones was 400° C., the linear velocity of gas phase was 0.3 m/s, the bed density was 1000 kg/m³, the average amount of carbon deposition in $1^{st}$ secondary pre-carbon deposition zone was 1 wt %, the average amount of carbon deposition in $1^{st}$ secondary reaction zone was 5 wt %, the average amount of carbon deposition in $2^{nd}$ secondary reaction zone was 8 wt %, and the average amount of carbon deposition in $3^{rd}$ secondary reaction zone was 10 wt %; the reaction conditions in the dense phase fluidized bed regenerator were as follows: the reaction temperature was 550° C., the linear velocity of gas phase was 0.3 m/s, the bed density was 1000 kg/m³, the average amount of carbon deposition in $1^{st}$ secondary regeneration zone was 5 wt %, the average amount of carbon deposition in $2^{nd}$ secondary regeneration zone was 2 wt %, the average amount of carbon deposition in $3^{rd}$ secondary regeneration zone was 0.5 wt %, and the average amount of carbon deposition in $4^{th}$ secondary regeneration zone was 0.02 wt %. The reaction product was analyzed by on-line gas phase chromatography, and the carbon-based yield of light olefin was 91.9 wt %.

EXAMPLE 2

1 secondary pre-carbon deposition zone and 2 secondary reaction zones were provided in the dense phase fluidized bed reactor and 2 secondary regeneration zones were provided in the dense phase fluidized bed regenerator. Hydrocarbon with four or more carbons etc. was passed into $1^{st}$ secondary pre-carbon deposition zone of the dense phase fluidized bed reactor, and was brought into contact with the completely regenerated catalyst, converting into a product comprising a light olefin, in the meantime, allowing the amount of carbon deposition on the catalyst reach to a certain value, to form a pre-carbon deposited catalyst, which was then passed into the reaction zone; a raw material comprising an oxygen-containing compound was passed in parallel into $1^{st}$ to $2^{nd}$ secondary reaction zone in the dense phase fluidized bed reactor, while the pre-carbon deposited catalyst was passed sequentially through $1^{st}$ to $2^{nd}$ secondary reaction zones, wherein the raw material comprising an oxygen-containing compound was brought into contact with the pre-carbon deposited catalyst, to generate a product comprising a light olefin and inactivated spent catalyst; the stream of gas phase product comprising a light olefin and the entrained spent catalyst are passed into a cyclone separator, from which, the gas phase product stream was passed into a subsequent separation section via the outlet of the cyclone separator, and the entrained spent catalyst was passed into $2^{nd}$ secondary reaction zone via the dipleg of the cyclone separator; via a stripper and a lift pipe, the spent catalyst from the $2^{nd}$ secondary reaction zone was passed into the dense phase fluidized bed regenerator, in which the spent catalyst was passed sequentially through $1^{st}$ to $2^{nd}$ secondary regeneration zone, and was brought into contact with the regeneration medium, resulting in the regenerated catalyst after reaction; the regenerated catalyst was passed into dense phase fluidized bed reactor again through a stripper and a lift pipe, and was passed sequentially through $1^{st}$ secondary pre-carbon deposition zone, $1^{st}$ secondary reaction zone and $2^{nd}$ secondary reaction zone; the byproduct of hydrocarbon with four or more carbons obtained from the separation section was returned back to $1^{st}$ secondary pre-carbon deposition zone in the dense phase fluidized bed reactor; the lifting gas in the lift pipe 15 was gasoline. The reaction conditions in the dense phase fluidized bed reactor were as follows: the temperature in $1^{st}$ secondary pre-carbon deposition zone was 550° C., the temperature in $1^{st}$ to $2^{nd}$ secondary reaction zones was 450° C., the linear velocity of gas phase was 0.5 m/s, the bed density was 900 kg/m³, the average amount of carbon deposition in $1^{st}$ secondary pre-carbon deposition zone was 2 wt %, the average amount of carbon deposition in $1^{st}$ secondary reaction zone was 6 wt %, and the average amount of carbon deposition in $2^{nd}$ secondary reaction zone was 8 wt %; the reaction conditions in the dense phase fluidized bed regenerator were as follows: the reaction temperature was 600° C., the linear velocity of gas phase was 0.7 m/s, the bed density was 700 kg/m³, the average amount of carbon deposition in $1^{st}$ secondary regeneration zone was 3 wt %, and the average amount of carbon deposition in $2^{nd}$ secondary regeneration zone was 0.1 wt %. The reaction product was analyzed by on-line gas phase chromatography, and the carbon-based yield of light olefin was 91.2 wt %.

EXAMPLE 3

1 secondary pre-carbon deposition zone and 5 secondary reaction zones were provided in the dense phase fluidized bed reactor and 5 secondary regeneration zones were provided in the dense phase fluidized bed regenerator. A mixture of naphtha and a hydrocarbon with four or more carbons was passed into $1^{st}$ secondary pre-carbon deposition zone of the dense phase fluidized bed reactor, and was brought into contact with the completely regenerated catalyst, converting into a product comprising a light olefin, in the meantime, allowing the amount of carbon deposition on the catalyst reach to a certain value, to form a pre-carbon deposited catalyst, which was then passed into the reaction zone; a raw material comprising an oxygen-containing compound was passed in parallel into $1^{st}$ to $5^{th}$ secondary reaction zones in the dense phase fluidized bed reactor, while the pre-carbon deposited catalyst was passed sequentially through $1^{st}$ to $5^{th}$ secondary reaction zones, wherein the raw material comprising an oxygen-containing compound was brought into contact with the pre-carbon deposited catalyst, to generate a product comprising a light olefin and inactivated spent catalyst; the stream of the gas phase product comprising a light olefin and the entrained spent catalyst were passed into a cyclone separator, from which, the gas phase product stream was passed into a subsequent separation section via the outlet of the cyclone separator, and the entrained spent catalyst was passed into $5^{th}$ secondary reaction zone via the dipleg of the cyclone separator; via a stripper and a lift pipe, the spent catalyst from the $5^{th}$ secondary reaction zone was passed into the dense phase fluidized bed regenerator, in which the spent catalyst was passed sequentially through $1^{st}$ to $5^{th}$ secondary regeneration zones, and was brought into contact with the regeneration medium, resulting in the regenerated catalyst after reaction; the regenerated catalyst was passed into dense phase fluidized bed reactor again through a stripper and a lift pipe, and was passed sequentially through $1^{st}$ secondary pre-carbon deposition zone, $1^{st}$ secondary reaction zone to $5^{th}$ secondary reaction zone; the byproduct of hydrocarbon with four or more carbons obtained from the separation section was returned back to $1^{st}$ secondary pre-carbon deposition zone in the dense phase fluidized bed reactor; the lifting gas in the lift pipe 15 was a hydrocarbon with four or more carbons. The reaction conditions in the dense phase fluidized bed reactor were as follows: the temperature in $1^{st}$ secondary pre-carbon deposition zone was 650° C., the temperature in $1^{st}$ to $5^{th}$ secondary reaction zones was 550° C., the linear velocity of gas phase was 0.7 m/s, the bed density was 700 kg/m$^3$, the average amount of carbon deposition in $1^{st}$ secondary pre-carbon deposition zone was 0.5 wt %, the average amount of carbon deposition in $1^{st}$ secondary reaction zone was 2.5 wt %, the average amount of carbon deposition in $2^{nd}$ secondary reaction zone was 4 wt %, the average amount of carbon deposition in $3^{rd}$ secondary reaction zone was 5 wt %; the average amount of carbon deposition in $4^{th}$ secondary reaction zone was 6 wt %, and the average amount of carbon deposition in $5^{th}$ secondary reaction zone was 7 wt %; the reaction conditions in the dense phase fluidized bed regenerator were as follows: the reaction temperature was 700° C., the linear velocity of gas phase was 1.0 m/s, the bed density was 500 kg/m$^3$, the average amount of carbon deposition in $1^{st}$ secondary regeneration zone was 5 wt %, the average amount of carbon deposition in $2^{nd}$ secondary regeneration zone was 3 wt %, the average amount of carbon deposition in $3^{rd}$ secondary regeneration zone was 1.5 wt %, the average amount of carbon deposition in $4^{th}$ secondary regeneration zone was 0.05 wt %, and the average amount of carbon deposition in $5^{th}$ secondary regeneration zone was 0.01 wt %. The reaction product was analyzed by on-line gas phase chromatography, and the carbon-based yield of light olefin was 92.5 wt %.

EXAMPLE 4

2 secondary pre-carbon deposition zones and 4 secondary reaction zones were provided in the dense phase fluidized bed reactor and 4 secondary regeneration zones were provided in the dense phase fluidized bed regenerator. Hydrocarbon with four or more carbons etc. was introduced in parallel into $1^{st}$ secondary pre-carbon deposition zone and $2^{nd}$ secondary pre-carbon deposition zone of the dense phase fluidized bed reactor, and was brought into contact with the completely regenerated catalyst, converting into a product comprising a light olefin, in the meantime, the catalyst was passed sequentially through $1^{st}$ secondary pre-carbon deposition zone and $2^{nd}$ secondary pre-carbon deposition zone, forming a pre-carbon deposited catalyst when the amount of carbon deposition reached to a certain value, which pre-carbon deposited catalyst was then passed into the reaction zone; a raw material comprising an oxygen-containing compound was passed in parallel into $1^{st}$ to $4^{th}$ secondary reaction zones in the dense phase fluidized bed reactor, while the pre-carbon deposited catalyst was passed sequentially through $1^{st}$ to $4^{th}$ secondary reaction zones, wherein the raw material comprising an oxygen-containing compound was brought into contact with the pre-carbon deposited catalyst, to generate a product comprising a light olefin and inactivated spent catalyst; the stream of the gas phase product comprising a light olefin and the entrained spent catalyst were passed into a cyclone separator, from which, the gas phase product stream was passed into a subsequent separation section via the outlet of the cyclone separator, and the entrained spent catalyst was passed into $4^{th}$ secondary reaction zone via the dipleg of the cyclone separator; via a stripper and a lift pipe, the spent catalyst from the $4^{th}$ secondary reaction zone was passed into the dense phase fluidized bed regenerator, in which the spent catalyst was passed sequentially through $1^{st}$ to $4^{th}$ secondary regeneration zones, and was brought into contact with the regeneration medium, resulting in the regenerated catalyst after reaction; the regenerated catalyst was passed into the dense phase fluidized bed reactor again through a stripper and a lift pipe, and was passed sequentially through $1^{st}$ secondary pre-carbon deposition zone, $2^{nd}$ secondary pre-carbon deposition zone, $1^{st}$ secondary reaction zone to $4^{th}$ secondary reaction zone; the byproduct of hydrocarbon with four or more carbons obtained from the separation section was returned back to $1^{st}$ secondary pre-carbon deposition zone and $2^{nd}$ secondary pre-carbon deposition zone in the dense phase fluidized bed reactor; the lifting gas in the lift pipe 15 was a hydrocarbon with four or more carbons. The reaction conditions in the dense phase fluidized bed reactor were as follows: the temperature in $1^{st}$ secondary pre-carbon deposition zone and $2^{nd}$ secondary pre-carbon deposition zone was 650° C., the temperature in $1^{st}$ to $4^{th}$ secondary reaction zones was 500° C., the linear velocity of gas phase was 1.0 m/s, the bed density was 500 kg/m$^3$, the average amount of carbon deposition in $1^{st}$ secondary pre-carbon deposition zone was 1.5 wt %, the average amount of carbon deposition in $2^{nd}$ secondary pre-carbon deposition zone was 3.0 wt %, the average amount of carbon deposition in $1^{st}$ secondary reaction zone was 4.5 wt %, the average amount of carbon deposition in $2^{nd}$ secondary reaction zone was 6.0 wt %, the average amount of carbon deposition in $3^{rd}$ secondary reaction zone was 7.0 wt %, and the average amount of carbon deposition in $4^{th}$ secondary reaction zone was 8.0 wt %; the reaction conditions in the dense phase fluidized bed regenerator were as follows: the reaction temperature was 700° C., the linear velocity of gas phase was 1.0 m/s, the bed density was 500 kg/m$^3$, the average amount of carbon deposition in $1^{st}$ secondary regeneration zone was 5.5 wt %, the average amount of carbon deposition in $2^{nd}$ secondary regeneration zone was 3 wt %, the average amount of carbon deposition in $3^{rd}$ secondary regeneration zone was 1.2 wt %, and the average amount of carbon deposition in $4^{th}$ secondary regeneration zone was 0.02 wt %. The reaction product was analyzed by on-line gas phase chromatography, and the carbon-based yield of light olefin was 93.2 wt %.

EXAMPLE 5

2 secondary pre-carbon deposition zones and 2 secondary reaction zones were provided in the dense phase fluidized bed reactor and 4 secondary regeneration zones were provided in the dense phase fluidized bed regenerator. Hydrocarbon with four or more carbons etc. was introduced in parallel into $1^{st}$ secondary pre-carbon deposition zone and $2^{nd}$ secondary pre-carbon deposition zone of the dense phase fluidized bed reactor, and was brought into contact with the completely regenerated catalyst, converting into a product comprising a light olefin, in the meantime, the catalyst was passed sequentially through $1^{st}$ secondary pre-carbon deposition zone and $2^{nd}$ secondary pre-carbon deposition zone, forming a pre-carbon deposited catalyst when the amount of carbon deposition reached to a certain value, which pre-carbon deposited catalyst was then passed into the reaction zone; a raw material comprising an oxygen-containing compound was passed in parallel into $1^{st}$ to $2^{nd}$ secondary reaction zones in the dense phase fluidized bed reactor, while the pre-carbon deposited catalyst was passed sequentially through $1^{st}$ to $2^{nd}$ secondary reaction zones, wherein the raw material comprising an oxygen-containing compound was brought into contact with the pre-carbon deposited catalyst, to generate a product comprising a light olefin and inactivated spent catalyst; the stream of the gas phase product comprising a light olefin and the entrained spent catalyst were passed into a cyclone separator, from which, the gas phase product stream was passed into a subsequent separation section via the outlet of the cyclone separator, and the entrained spent catalyst was passed into $2^{nd}$ secondary reaction zone via the dipleg of the cyclone separator; via a stripper and a lift pipe, the spent catalyst from the $2^{nd}$ secondary reaction zone was passed into the dense phase fluidized bed regenerator, in which the spent catalyst was passed sequentially through $1^{st}$ to $4^{th}$ secondary regeneration zones, and was brought into contact with the regeneration medium, resulting in the regenerated catalyst after reaction; the regenerated catalyst was passed into the dense phase fluidized bed reactor again through a stripper and a lift pipe, and was passed sequentially through $1^{st}$ secondary pre-carbon deposition zone, $2^{nd}$ secondary pre-carbon deposition zone, $1^{st}$ secondary reaction zone, and $2^{nd}$ secondary reaction zone; the byproduct of hydrocarbon with four or more carbons obtained from the separation section was returned back to $1^{st}$ secondary pre-carbon deposition zone and $2^{nd}$ secondary pre-carbon deposition zone in the dense phase fluidized bed reactor; the lifting gas in the lift pipe 15 was a hydrocarbon with four or more carbons. The reaction conditions in the dense phase fluidized bed reactor were as follows: the temperature in $1^{st}$ secondary pre-carbon deposition zone and $2^{nd}$ secondary pre-carbon deposition zone was 650° C., the temperature in $1^{st}$ to $2^{nd}$ secondary reaction zones was 500° C., the linear velocity of gas phase was 1.0 m/s, the bed density was 500 kg/m³, the average amount of carbon deposition in $1^{st}$ secondary pre-carbon deposition zone was 1.5 wt %, the average amount of carbon deposition in $2^{nd}$ secondary pre-carbon deposition zone was 3.0 wt %, the average amount of carbon deposition in $1^{st}$ secondary reaction zone was 6.0 wt %, and the average amount of carbon deposition in $2^{nd}$ secondary reaction zone was 8.5 wt %; the reaction conditions in the dense phase fluidized bed regenerator were as follows: the reaction temperature was 700° C., the linear velocity of gas phase was 1.0 m/s, the bed density was 500 kg/m³, the average amount of carbon deposition in $1^{st}$ secondary regeneration zone was 8 wt %, the average amount of carbon deposition in $2^{nd}$ secondary regeneration zone was 3 wt %, the average amount of carbon deposition in $3^{rd}$ secondary regeneration zone was 1 wt %, the average amount of carbon deposition in $4^{th}$ secondary regeneration zone was 0.02 wt %. The reaction product was analyzed by on-line gas phase chromatography, and the carbon-based yield of light olefin was 92.8 wt %.

The present invention has been described in detail above, but the invention is not limited to the specific embodiments described herein. It will be appreciated by those skilled in the art that other modifications and variations can be made without departing from the scope of the invention. The scope of the invention is defined by the appended claims.

What is claimed is:

1. A method for preparing a light olefin using an oxygen-containing compound, comprising the following steps:
    step a) in which a hydrocarbon with four or more carbons is introduced from k feeding branch lines of pre-carbon deposition zone in parallel into k secondary pre-carbon deposition zones in a dense phase fluidized bed reactor, and is brought into contact with a completely regenerated and/or fresh catalyst, so as to be converted into a light olefin product-containing stream, while forming a pre-carbon deposited catalyst; wherein the catalyst is passed sequentially through $1^{st}$ to $k^{th}$ secondary pre-carbon deposition zones, with carbon content thereof increasing gradually; wherein the dense phase fluidized bed reactor is divided by a material flow controller into a pre-carbon deposition zone and a reaction zone; and wherein the pre-carbon deposition zone of the dense phase fluidized bed reactor is divided by a material flow controller into k secondary pre-carbon deposition zones, with $1^{st}$ to $k^{th}$ secondary pre-carbon deposition zones being connected in sequence;
    step b) in which a raw material comprising the oxygen-containing compound is introduced from n feeding branch lines of reaction zone in parallel into n secondary reaction zones of the dense phase fluidized bed reactor, and is brought into contact with the pre-carbon deposited catalyst, to generate a light olefin product-containing stream and a spent catalyst; wherein the pre-carbon deposited catalyst flowed out from the $k^{th}$ secondary pre-carbon deposition zone is passed sequentially through $1^{st}$ to $n^{th}$ secondary reaction zones, with carbon content thereof increasing gradually; wherein the reaction zone of the dense phase fluidized bed reactor is divided by a material flow controller into n secondary reaction zones, with $1^{st}$ to $n^{th}$ secondary reaction zones being connected in sequence, and the $1^{st}$ secondary reaction zone being connected to the downstream of the $k^{th}$ secondary pre-carbon deposition zone;
    step c) in which the light olefin product-containing stream flowed out from the pre-carbon deposition zone and the reaction zone is separated from the entrained spent catalyst; the isolated spent catalyst is passed into the $n^{th}$ secondary reaction zone; and the light olefin product-containing stream is passed into a product separation section, in which the light olefin product is obtained by isolation and purification, and the hydrocarbon byproduct with four or more carbons obtained from the separation section is returned back to the pre-carbon deposition zone in the dense phase fluidized bed reactor; and
    step d) in which the spent catalyst flowed out from the $n^{th}$ secondary reaction zone, after being stripped and lifted, is passed into a dense phase fluidized bed regenerator for regeneration; said spent catalyst is passed sequentially through $1^{st}$ to $m^{th}$ secondary regeneration zones; a regeneration medium is introduced in parallel from m feeding branch lines of regeneration zone into the $1^{st}$ to $m^{th}$ secondary regeneration zones, and the spent catalyst is brought into contact with the regeneration medium, with the carbon content thereof decreasing gradually; the catalyst after the completion of regeneration is returned back to the $1^{st}$ secondary pre-carbon deposition zone via stripping and lifting; wherein the dense phase fluidized bed regenerator is divided by a material flow controller into m secondary regeneration zones, and $1^{st}$ to $m^{th}$ secondary regeneration zones are connected in sequence;
    wherein $k \geq 1$, $n \geq 1$, and $m \geq 2$.

2. The method according to claim 1, wherein $4 \geq k \geq 2$, $8 \geq n \geq 3$, and $8 \geq m \geq 3$.

3. The method according to claim 1, wherein, in the dense phase fluidized bed reactor, the apparent linear velocity of gas in the material flow controller is less than or equals to the minimum fluidizing velocity of the catalyst.

4. The method according to claim 1, wherein, in the dense phase fluidized bed regenerator, the apparent linear velocity of gas in the material flow controller is less than or equals to the minimum fluidizing velocity of the catalyst.

5. The method according to claim 1, wherein the catalyst comprises SAPO-34 molecular sieve.

6. The method according to claim 1, wherein the reaction conditions in the dense phase fluidized bed reactor are as follows: the apparent linear velocity of gas in the pre-carbon deposition zone and the reaction zone is 0.1-1.5 m/s, the reaction temperature in the pre-carbon deposition zone is 500-650° C., the temperature in the reaction zone is 400-550° C., and the bed density in the dense phase fluidized bed reactor is 200-1200 kg/m$^3$.

7. The method according to claim 1, wherein the average amount of carbon deposition on catalyst is increased in sequence from the $1^{st}$ secondary pre-carbon deposition zone to the $n^{th}$ secondary reaction zone in the dense phase fluidized bed reactor, wherein the average amount of carbon deposition on catalyst in the $k^{th}$ secondary pre-carbon deposition zone is 0.5-3 wt %, and the average amount of carbon deposition on catalyst in the $n^{th}$ secondary reaction zone is 7-10 wt %.

8. The method according to claim 1, wherein the reaction conditions in the regeneration zone of the dense phase fluidized bed are as follows: the apparent linear velocity of gas is 0.1-1.5 m/s, the reaction temperature is 500-700° C., and the bed density is 200-1200 kg/m$^3$.

9. The method according to claim 1, wherein the average amount of carbon deposition on catalyst is decreased in sequence from the $1^{st}$ to $m^{th}$ secondary regeneration zones in the dense phase fluidized bed regeneration zone, wherein the average amount of carbon deposition on catalyst in the $1^{st}$ secondary regeneration zone is 2-10 wt %, and the average amount of carbon deposition on catalyst in the $m^{th}$ secondary regeneration zone is 0-0.1 wt %.

10. The method according to claim 1, wherein the oxygen-containing compound is methanol and/or dimethyl ether.

11. The method according to claim 1, wherein the catalyst after the completion of regeneration in step d) is subsequently returned back to the $1^{st}$ secondary pre-carbon deposition zone of the dense phase fluidized bed via stripping and lifting, wherein the lifting gas in the lifting process is any one of water vapor, a hydrocarbon with four or more carbons, naphtha, gasoline, condensate oil, light diesel oil, hydrogenation tail oil or kerosene, or a mixture thereof.

12. The method according to claim 1, wherein the light olefin is any one of ethylene, propylene or butylene, or a mixture thereof.

13. The method according to claim 1, wherein the hydrocarbon with four or more carbons is any one of naphtha, gasoline, condensate oil, light diesel oil, hydrogenation tail oil or kerosene, or a mixture thereof.

14. The method according to claim 1, wherein the regeneration medium is any one of air, oxygen-deficient air or water vapor, or a mixture thereof.

* * * * *